United States Patent [19]
Haugen

[11] Patent Number: 5,318,068

[45] Date of Patent: Jun. 7, 1994

[54] CAST SUPPORT DEVICE

[76] Inventor: Larry D. Haugen, 8162 Somerset Rd., Woodbury, Minn. 55125

[21] Appl. No.: 126,701

[22] Filed: Sep. 20, 1993

[51] Int. Cl.$^5$ .............................................. A45B 3/00
[52] U.S. Cl. ........................................ 135/66; 135/68
[58] Field of Search ................. 135/66, 68, 65, 67, 135/69, 74

[56] References Cited

U.S. PATENT DOCUMENTS

| | | | |
|---|---|---|---|
| 979,959 | 12/1910 | Johnson | 135/66 X |
| 3,999,565 | 12/1976 | Delacour et al. | 135/65 |
| 4,291,715 | 9/1981 | Monte | 135/68 |
| 4,910,927 | 3/1990 | Beatty | 135/68 |

FOREIGN PATENT DOCUMENTS

| | | | |
|---|---|---|---|
| 0497013 | 11/1919 | France | 135/68 |
| 114399 | 4/1918 | United Kingdom | 135/68 |

Primary Examiner—Carl D. Friedman
Assistant Examiner—Lan C. Mai
Attorney, Agent, or Firm—Herman H. Bains

[57] ABSTRACT

A device for supporting the leg cast includes a cast engaging member which engages and supports the leg cast of person. In one embodiment, the device is attached to a crutch and is shiftable between collapsed and erect positions. In another embodiment, the device is attached to the cast itself and is shiftable between collapsed and erect positions. When the device is in the erect position, the cast of a user will be supported thereon when the user is in a sitting position. When the device is in the collapsed position, it is suspended vertically in an out-of-way position from the cast or crutch of the user.

6 Claims, 3 Drawing Sheets

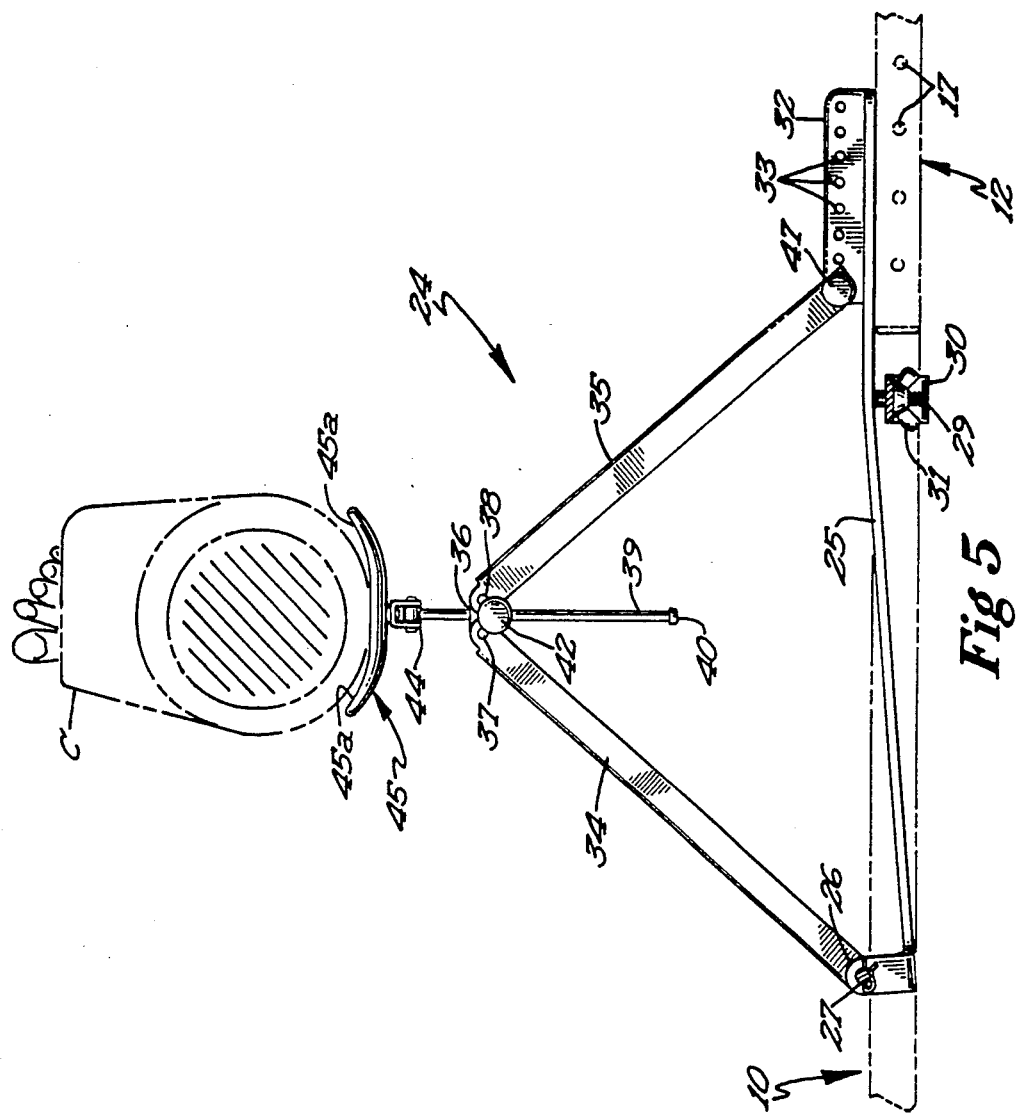
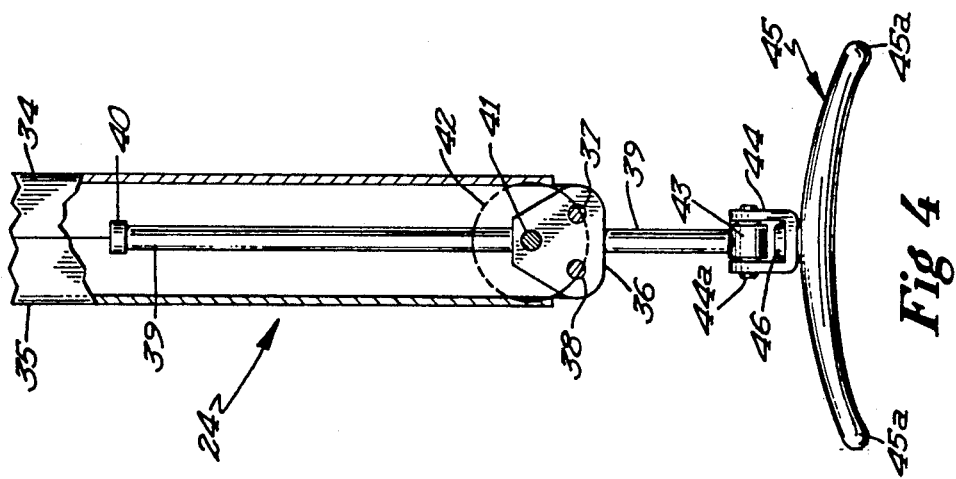

CAST SUPPORT DEVICE

FIELD OF THE INVENTION

This invention relates to a cast support device.

BACKGROUND OF THE INVENTION

Persons with leg injuries are often provided with a cast to immobilize the injured leg. People having leg casts experience discomfort when sitting down. This discomfort is relieved if the person is able to elevate the leg which bears the cast.

In many instances, there are no available objects (such as stools, chairs and similar devices) for supporting the person's leg in an elevated position. Many persons with injured legs use crutches to assist them. Other persons having injured legs are provided with a walking cast and choose not to use crutches.

SUMMARY OF THE INVENTION

It is an object of this invention to provide a cast support device which is attached to a conventional crutch and which serves to support the cast bearing leg of a person when the person is in a sitting position.

Another object of this invention is the provision of a cast support device which is detachably secured to a walking cast and which is operable to support the wearer's leg in an elevated position when the wearer is in the sitting position.

In one embodiment of the invention, the cast support device is attached to a conventional crutch and is shiftable between a collapsed position and an erect position. When the cast device is in the collapsed position, it is suspended in close proximal relation with respect to the crutch. When the cast support device is in the erect position, it extends upwardly from the crutch when the latter is lying on a floor.

In another embodiment of the invention, the cast support device is detachably strapped to the cast of a wearer and is erected from a collapsed position to support the leg of the wearer in an elevated position when the wearer is in a sitting position.

BRIEF DESCRIPTION OF THE DRAWING

FIG. 4 is a cross-sectional view taken approximately along line 4—4 of FIG. 3 and looking in the direction of the arrows;

FIG. 5 is a fragmentary elevational view illustrating the cast support device in an erect position;

DESCRIPTION OF THE PREFERRED EMBODIMENT

Figure 1:
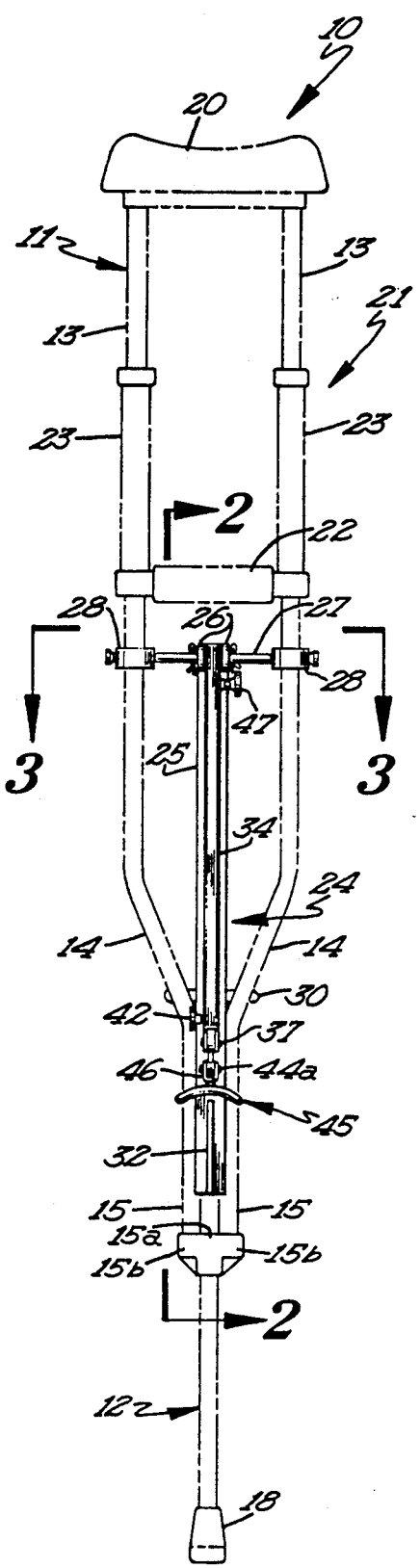
FIG. 1 is a side elevational view of one embodiment of the novel cast support device attached to a conventional crutch, the latter being illustrated by phantom line configuration.

Referring now to the drawings and more specifically to FIG. 1, it will be seen that the novel cast support device, designated generally by the reference numeral 24, is illustrated in mounted relation on a conventional crutch 10. The crutch 10 is preferably formed of a light weight metallic material such as aluminum or the like and includes a pair of elongate similar upper crutch members 11 which are adjustably connected to an elongate lower crutch member 12. Each upper crutch member 11 includes an upper portion 13 and an intermediate portion 14 which extends angularly from the upper portion and terminates in a lower portion 15.

It will be noted that the respective upper portions 13 of the upper crutch members and the respective lower portions 15 thereof are disposed of in substantially parallel relation while the intermediate portions 14 converge downwardly towards each other. The lower crutch member 12 is provided with a plurality of openings 17 therein for accommodating a nut and bolt assembly 16 to permit vertical adjustment of the upper and lower crutch members relative to each other in well known way.

The lower end of the lower crutch member 12 is provided with a ground engaging anti-skid element 18 and the upper end of the upper crutch members is provided with a shoulder rest 19. A cushion type cover 20 formed of sponge rubber or the like is positioned on the shoulder rest 19. The crutch 10 also includes a vertically adjustable hand hold assembly 21 including a hand hold member 22 which extends transversely of the upper crutch members 11. The hand hold member 22 is provided with a cover formed of soft plastic or rubber material and is adapted to be gripped by a user. The hand hold member 22 is connected to a pair of elongate vertical slides 23 which are shiftable relative to the upper portions 13 of the upper crutch members. In this regard, the upper portions 13 of the upper crutch members are provided with a detent or detents for engaging in openings in the slides in a well known manner. The crutch 10 is of conventional construction and does not per se form part of the present invention.

The cast support device 24 includes an elongate base member 25 having a pair of spaced apart ears 26 integrally formed with the upper end thereof. The ears 26 are provided with openings therein for receiving a rod 27 therethrough, the ends of the rod being secured to clips 28 which engage the upper portions 13 of the upper crutch members below the hand hold assembly 21. The base member 25 is also provided with a threaded stud member 29 intermediate in its ends and the threaded stud member is engaged by a wing nut 31 for clamping a bar 30 against the upper crutch members 11. The lower end portion of the base member 25 is provided with a pin 25a which engages in an opening in the lower crutch member 12.

Figure 2:
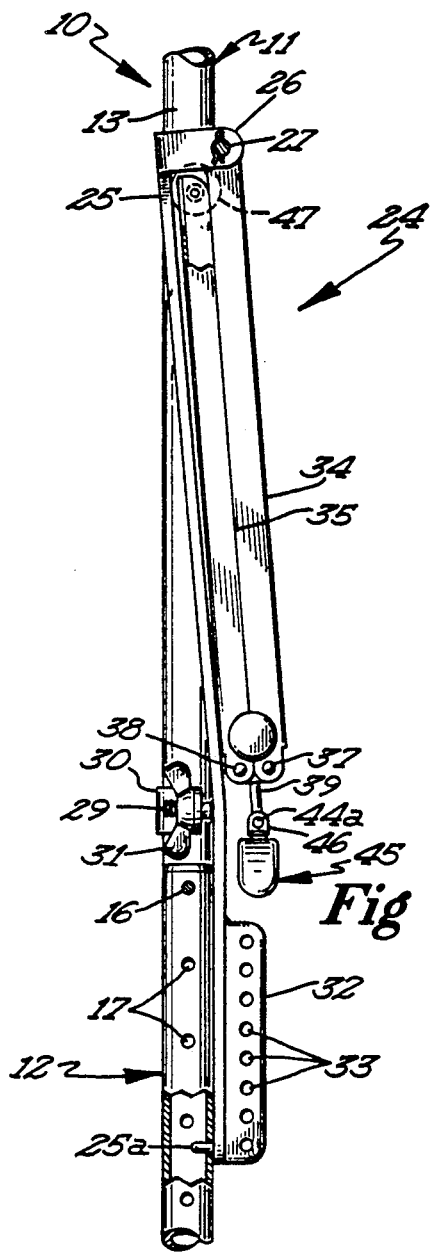
FIG. 2 is a cross-sectional view taken approximately along line 2—2 of FIG. 1 and looking in the direction of the arrows.
Figure 3:
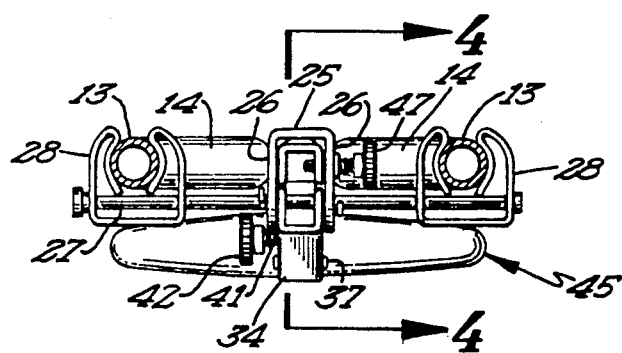
FIG. 3 is a cross-sectional view taken approximately along line 3—3 of FIG. 1 and looking in the direction of the arrows.
Figure 6:
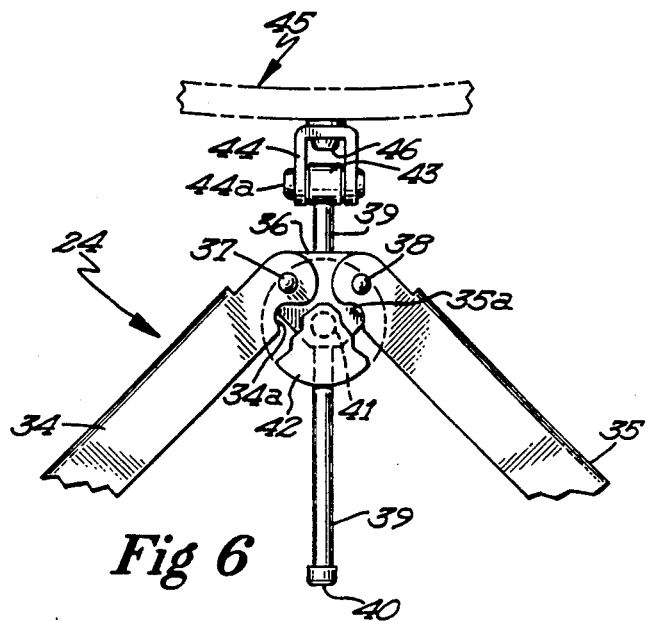
FIG. 6 is a view similar to FIG. 4 but illustrating the position of various components of the cast support device when the latter is in an erect position.

An elongate substantially rectangular shaped flat bar 32 is rigidly secured to the base member 25 adjacent the lower end thereof. The bar 32 has a plurality of spaced apart openings 33 therein throughout its length as best seen in FIG. 2.

The cast support device 24 also includes a first link 34 which is pivotally interconnected to a second link 35 by a coupling member 36. It will be seen that one end of the first link 34 is journaled on the rod 27 for pivotal movement relative thereto.

The other end of the first link 34 is pivotally connected to the coupling member 36 by pivot 37. The second link 35 has one end thereof pivotally connected to the coupling member 36 by a pivot 38. It will be noted that the other end of second link 35 is secured to locking bar 32 by a locking element 47 that passes through one of the openings 33 therein.

The coupling member 36 has a bore therethrough for slideably accommodating an elongate rod 39 therein. One end of the rod 39 is provided with a stop element 40, and the rod may be selectively adjusted relative to the coupling member 36 by set screw 41 having a knob 42 secured thereto. The other end of the rod 39 has a sleeve element 43 rigidly secured thereto. A U-shaped member 44 is pivotally secured to the sleeve element 43 by a pin 44a which extends through the sleeve element. A cast engaging member 45 is pivotally secured to the U-shaped member 44 by pivot 46. Although not shown, friction elements yieldably resist pivotal movement of the U-shaped member about pivot 44a. The cast engaging member is of concavo-convex configuration, and the concave side 45a is the surface engaged by the cast of a wearer.

The cast support device 24 is shiftable between a collapsed position, as illustrated in FIG. 2, and an erect position, as illustrated in FIG. 5. When the cast support device 24 is in the collapsed position, it is disposed in suspended relation from the crutch and does not interfere with the use of the crutch in any manner. On the other hand, when the cast support device is in the erect position, the crutch will be lying upon a surface, such as a floor, and the second link 35 of the cast support device will be interlocked with the locking bar 32 so that the cast support device assumes the configuration as illustrated in FIG. 5. The cast engaging member will be positioned so that the concave surface 45 thereof will be facing upwardly to permit the leg cast of wearer to engage the concave surface of the cast engaging member.

The rod 39 may be vertically adjusted relative to the coupling member 36 by loosening the set screw 41 via the knob 42 and vertically shifting the rod relative to the coupling member. With this arrangement, the crutch serves as carrier and support for the cast support device 24.

Figure 7:
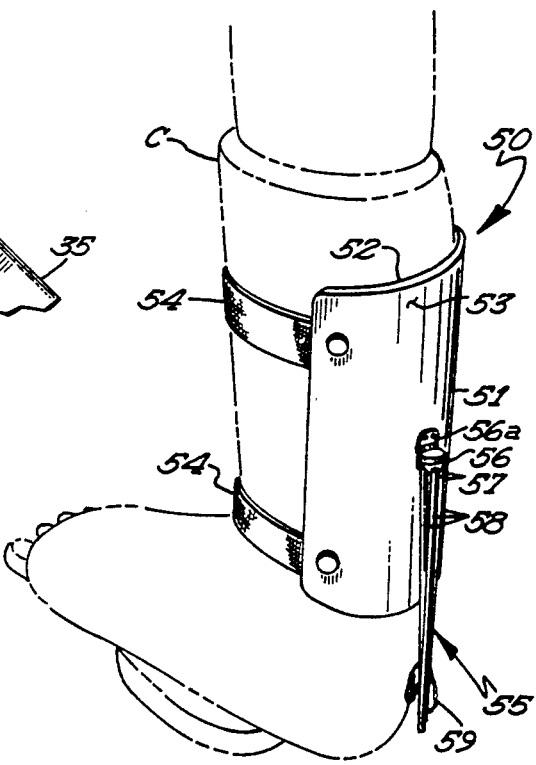
FIG. 7 is a rear perspective view of a different embodiment of the cast support device illustrated in the collapsed position and attached to a cast.
Figure 8:
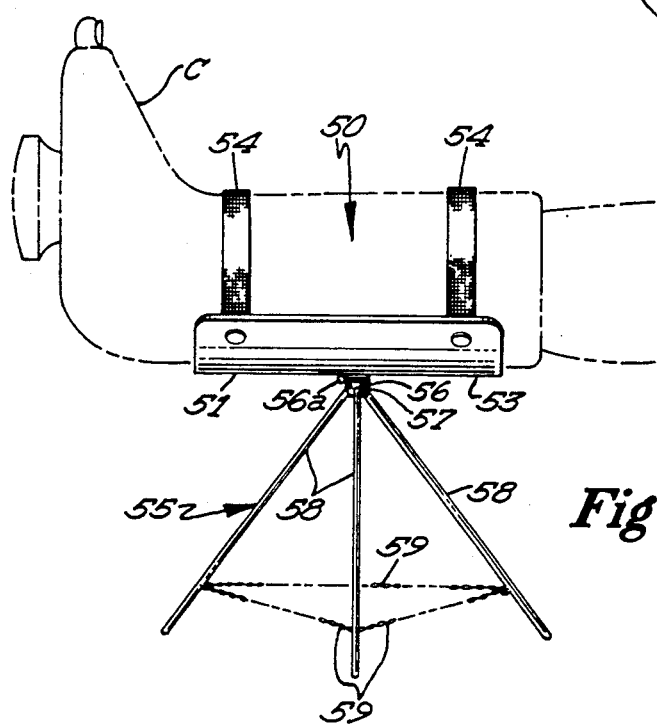
FIG. 8 is a side elevational view illustrating the cast support device of FIG. 7 in an erect elevated position.

Referring now to FIGS. 7 and 8, it will be seen that a modified form of the cast support device, designated generally by the reference numeral 50 is thereshown. The cast support device 50 is detachably secured to a walking cast C. The cast support device is readily shiftable between a collapsed position, as illustrated in FIG. 7, and an erect position, as illustrated in FIG. 8. The cast support device 50 is illustrated in use with a relatively short walking type cast C and includes a convavo-convex elongate cast engaging member 51. The cast engaging member 51 includes a concave inner or upper surface 52 and a convex outer or lower surface 53. The cast engaging member may be formed of a suitable rigid plastic material and is readily secured to the cast C of a user by means of a pair of flexible straps 54. Each pair of straps 54 are interconnected to its associated mate by velcro fastening means or buckles in a well known manner.

The cast engaging member 51 also includes a collapsible support 55 comprised of a mounting member 56 hingedly connected to the convex surface 53 of the cast engaging member intermediate the ends of the latter by a hinge 56a. The mounting member 56 is provided with a plurality of socket openings 57 therein for accommodating one end of each of a plurality of elongate legs 58 therein. The legs are pivoted between a collapsed position, as illustrated in FIG. 7, and an erect position, as illustrated in FIG. 5. In the embodiment shown, shifting movement of the legs 58, when in the erect position, is restrained by flexible restraining elements 59 which extend between adjacent pairs of legs 58. The flexible restraining elements 59 hold the loegs in proper angular position. In the embodiment shown, three such legs are used with the cast engaging member.

In use, the user will shift the collapsible support 55 to the collapsed position when walking but will shift the collapsible support to the erect position when the user is in the sitting position. It will be noted that in both embodiments, the user will have the cast bearing leg elevated when in the sitting position to thereby relieve the user of any discomfort associated with a cast resting on the floor.

Thus it will be seen that I have provided a novel cast support device, which is not only of simple and inexpensive construction, but one which functions in a more efficient manner than any heretofore known comprable device.

What is claimed is:

1. In combination with an elongate vertically adjustable crutch including an upper crutch member and a lower crutch member interconnected together for extension and retraction relative to each other, a shoulder rest on the upper end of the upper crutch member, a hand hold on said upper crutch member located below said shoulder rest, a cast support shiftably mounted on said crutch and being shiftable between erect and collapsed positions, said cast support including first and second elongate support links, said first link having one end thereof pivotally connected to said crutch, means pivotally interconnecting the other end of said first link with one end of said second link, releasable locking elements connected with said crutch and said second link adjacent the other end thereof, said locking elements engaging each other to releasably lock the support links in the erect position extending angularly upwardly from the crutch when the latter is disposed on a flat surface such as a floor, said locking elements when released permitting said links to be suspended vertically in side-by-side relation, and a cast engaging member, means connecting the cast engaging member to said links adjacent the interconnected ends thereof, said casting engaging member engaging the cast of a user when the cast support is in the erect position.

2. The invention as defined in claim 1 wherein said cast support is vertically adjustable relative to the crutch when the cast support is in the erect position.

3. The invention as defined in claim 1 wherein said means connecting said cast engaging member with said links includes a pivot to permit pivotal movement of the cast engaging member about a vertical axis when the cast support is in the erect position.

4. The invention as defined in claim 1 wherein said locking element connected with said crutch includes an elongate apertured bar, and means on said second link engaging one of the apertures in said bar.

5. The invention as defined in claim 1 wherein said cast support includes an elongate base plate, means releasably securing said base plate to said crutch, and said first link having said one end pivotally connected to said base plate.

6. The invention is defined in claim 5 wherein said locking means connected with said crutch includes a locking bar mounted on said base plate.

* * * * *